(12) United States Patent
Cooke et al.

(10) Patent No.: US 11,413,284 B2
(45) Date of Patent: Aug. 16, 2022

(54) PROTEIN KINASE C INHIBITORS FOR TREATMENT OF UVEAL MELANOMA

(71) Applicant: NOVARTIS AG, Basel (CH)

(72) Inventors: Vesselina Cooke, Cambridge, MA (US); Michael Scott Visser, Cambridge, MA (US); Andrew Wylie, Newton, MA (US); Padmaja Yerramilli-Rao, Cambridge, MA (US); Xu Zhu, Cambridge, MA (US)

(73) Assignee: Novartis AG, Basel (CH)

( * ) Notice: Subject to any disclaimer, the term of this patent is extended or adjusted under 35 U.S.C. 154(b) by 28 days.

(21) Appl. No.: 16/646,390

(22) PCT Filed: Sep. 11, 2018

(86) PCT No.: PCT/IB2018/056945
§ 371 (c)(1),
(2) Date: Mar. 11, 2020

(87) PCT Pub. No.: WO2019/053595
PCT Pub. Date: Mar. 21, 2019

(65) Prior Publication Data
US 2020/0268749 A1 Aug. 27, 2020

Related U.S. Application Data

(60) Provisional application No. 62/557,520, filed on Sep. 12, 2017.

(51) Int. Cl.
*A61K 31/497* (2006.01)
*A61P 35/00* (2006.01)
*A61K 9/00* (2006.01)
*A61K 45/06* (2006.01)

(52) U.S. Cl.
CPC .......... *A61K 31/497* (2013.01); *A61K 9/0053* (2013.01); *A61K 45/06* (2013.01); *A61P 35/00* (2018.01)

(58) Field of Classification Search
CPC .................................................... A61K 31/497
USPC .................................................... 514/255.05
See application file for complete search history.

(56) References Cited

U.S. PATENT DOCUMENTS

2016/0347737 A1* 12/2016 Luzzio ................. A61K 31/497

FOREIGN PATENT DOCUMENTS

| WO | WO 2011/076786 A1 | 6/2011 |
| WO | WO 2012/066095 A1 | 5/2012 |
| WO | WO 2013/111105 A1 | 8/2013 |
| WO | WO 2017/029588 A2 | 2/2017 |

OTHER PUBLICATIONS

ClinicalTrials.gov: NCT02601378, Nov. 10, 2015.*
Houben et al., PloS One (2011), vol. 6(7), e22096, pp. 1-7.*
International Search Report and Written Opinion for Corresponding International Application No. PCT/IB18/056945, dated Mar. 21, 2019, 12 pages.
Davies et al., "PERP expression stabilizes active p53 via modulation of p53-MDM2 interaction in uveal melanoma cells." Cell death & disease vol. 2,3 e136. Mar. 31, 2011.
de Lange et al., "Synergistic growth inhibition based on small-molecule p53 activation as treatment for intraocular melanoma." Oncogene 31, 1105-1116 (2012).
Harbour, "The genetics of uveal melanoma: an emerging framework for targeted therapy." Pigment cell & melanoma research vol. 25,2 (2012): 171-81.
Mochly-Rosen et al., "Protein kinase C, an elusive therapeutic target?." Nature reviews. Drug discovery vol. 11,12 (2012): 937-57.
Novartis Pharmaceuticals: A Phase I Study of LXS196 in Patients with Metastatic Uveal Melanoma.—ClinicalTrials.gov, Nov. 10, 2015, XP055523018 NCT02601378.
Patel et al., "Small-molecule inhibitors of the p53-HDM2 interaction for the treatment of cancer." Expert opinion on investigational drugs vol. 17,12 (2008): 1865-82.
Piperno-Neumann et al. A phase I trial of LXS196, Pigment cell & melanoma research, vol. 31, No. 1. (2018): 196.

* cited by examiner

*Primary Examiner* — Taofiq A Solola
(74) *Attorney, Agent, or Firm* — Brian C. Trinque; Nicole Sassu; Lathrop GPM LLP

(57) ABSTRACT

The present disclosure relates to use of a protein kinase C (PKC) inhibitor in the treatment or prevention of proliferative diseases. The disclosure also relates to corresponding pharmaceutical formulations, uses, methods, combinations, and related disclosure embodiments. The disclosure further relates to use of a pharmaceutical combination comprising a PKC inhibitor and another therapeutic agent, such as an MDM2 inhibitor, in the treatment or prevention of a proliferative disease.

16 Claims, No Drawings

PROTEIN KINASE C INHIBITORS FOR TREATMENT OF UVEAL MELANOMA

RELATED APPLICATIONS

This application claims priority to, and the benefit of, U.S. Application Ser. No. 62/557,520, filed Sep. 12, 2017, the content of which is hereby incorporated by reference in its entirety.

BACKGROUND

Uveal melanoma (UM) is the most common cancer of the eye in adults (Singh A D. et al., Ophthalmology. 2011; 118: 1881-5). Most UM patients develop metastases for which no curative treatment has been identified so far.

The majority of UM tumors have mutations in the genes GNAQ (guanine nucleotide-binding protein G(q) subunit alpha) and GNA11 (guanine nucleotide-binding protein G(q) subunit 11), which encode for small GTPases (Harbour J W. Pigment Cell Melanoma Res. 2012; 25:171-81). Both of these mutations lead to activation of the protein kinase C (PKC) pathway. The up-regulation of PKC pathway has downstream effects which leads to constitutive activation of the mitogen-activated protein kinase (MAPK) signaling pathway that has been implicated in causing uncontrolled cell growth in a number of proliferative diseases.

Whilst anti-proliferative effects have been observed with certain PKC pathway inhibitors, no sustained MAPK pathway inhibition has been observed. Thus far, PKC inhibitors (PKCi) have had limited efficacy as single agents in patients (Mochly-Rosen D et al., Nat Rev Drug Discov. 2012 December; 11(12):937-57). There still remains an unmet need to provide next generation PKC inhibitors for treating uveal melanoma.

SUMMARY

In one aspect, the present disclosure features a method for the treatment or prevention of a proliferative disease, e.g., uveal melanoma, in a subject in need thereof. The method includes administration of a therapeutically effective amount of a protein kinase C inhibitor (PKCi) in said subject.

The method can include one or more of the following features.

In certain embodiments, the PKC inhibitor is 3-amino-N-(3-(4-amino-4-methylpiperidin-1-yl)pyridin-2-yl)-6-(3-(trifluoromethyl)pyridin-2-yl)pyrazine-2-carboxamide (Compound I) or a pharmaceutically acceptable salt thereof.

In certain embodiments, the PKC inhibitor is administered orally.

In certain embodiments, the PKC inhibitor is administered on an empty stomach, such as at least 1 hour before or 2 hours after a meal. For example, water and other medications may be permitted during this period. In other embodiments, the PKC inhibitor is administered immediately prior to or after the subject eats some food.

In certain embodiments, the method includes administering to a subject in need of thereof 3-amino-N-(3-(4-amino-4-methylpiperidin-1-yl)pyridin-2-yl)-6-(3-(trifluoromethyl)pyridin-2-yl)pyrazine-2-carboxamide (Compound I) or a pharmaceutically acceptable salt thereof at a dose of from about 100 mg to about 1000 mg of Compound I daily.

In certain embodiments, Compound I or a pharmaceutically acceptable salt thereof is administered at a dose of between about 50 mg twice a day (BID) and about 400 mg BID of Compound I (e.g., at a dose of about 50 mg BID, 100 mg BID, 150 mg BID, 200 mg BID, 250 mg BID, 300 mg BID, 350 mg BID, or 400 mg BID).

In certain embodiments, Compound I or a pharmaceutically acceptable salt thereof is administered at a dose of about 300 mg BID of Compound I.

In certain embodiments, Compound I or a pharmaceutically acceptable salt thereof is administered at a dose of from about 100 mg to about 1000 mg of Compound I once daily (e.g., about 400 mg, 500 mg, 600 mg, 700 mg or about 800 mg once daily).

In certain embodiments, the subject suffers from metastatic uveal melanoma.

In certain embodiments, the subject is a human being, e.g., an adult patient aged 18 years or older.

In certain embodiments, Compound I or a pharmaceutically acceptable salt thereof is orally administered.

In certain embodiments, the method further includes administering to the subject one or more other therapeutic agents, e.g., a mouse double minute 2 inhibitor (MDM2i or HDM2i). MDM2 and HDM2, the human isoform of MDM2, are used interchangeably herein.

In certain embodiments, the method further includes administering to the subject a mouse double minute 2 inhibitor (MDM2i) selected from (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Compound II), (S)-1-(4-chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound III), and pharmaceutically acceptable salts thereof.

In certain embodiments, the method further includes administering to the subject (S)-1-(4-chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (Compound III), or a pharmaceutically acceptable salt thereof, for example, orally.

In certain embodiments, the method further includes administering to the subject (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Compound II), or a pharmaceutically acceptable salt thereof, for example, orally.

In certain embodiments, the method further includes administering to the subject (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Compound II), or a pharmaceutically acceptable salt thereof once weekly, for example, orally.

In certain embodiments, Compound II or a pharmaceutically acceptable salt thereof is administered at a dose of from about 50 mg to about 200 mg of Compound II (e.g., at a dose of about 50 mg, about 80 mg, about 100 mg, about 120 mg, about 150 mg, or about 200 mg of Compound II).

In certain embodiments, Compound II or III, or a pharmaceutically acceptable salt thereof is orally administered.

In certain embodiments, Compound II or III, or a pharmaceutically acceptable salt thereof, is administered on an empty stomach, such as at least 1 hour before or 2 hours after a meal. For example, water and other medications may be permitted during this period. In other embodiments, Compound II or III, or a pharmaceutically acceptable salt thereof, is administered immediately prior to or after the subject eats some food.

In certain embodiments, the uveal melanoma or metastatic uveal melanoma comprises functional p53 or wild-type TP53.

In certain embodiments, the uveal melanoma or metastatic uveal melanoma is characterized by mutation of guanine nucleotide-binding protein G(q) subunit alpha (GNAQ) gene or guanine nucleotide-binding protein G(q) subunit 11 (GNA11) gene.

The following disclosure pertains to dually targeting p53, either alone or in combination with the PKC pathway in order to treat UM. In this way, the MDM2 inhibitor promotes the beneficial effect of another compound that targets a possibly subordinate, interdependent or simply coexisting biochemical pathway implicated in causing a proliferative disease.

In another aspect, the present disclosure features a PKC inhibitor for use in treating or preventing a proliferative disease, e.g., uveal melanoma, either alone or in a combination therapy with one or more other therapeutic agents such as an MDM2 inhibitor. For example, the PKC inhibitor is Compound I or a pharmaceutically acceptable salt thereof. For example, the PKC inhibitor is suitable for administration at a dose of from about 100 mg to about 1000 mg of Compound I daily, e.g., via oral administration. For example, the PKC inhibitor is administered on an empty stomach, such as at least 1 hour before or 2 hours after a meal.

In yet another aspect, the present disclosure features use of a PKC inhibitor in the manufacture of a medicament for the treatment or prevention of a proliferative disease, e.g., uveal melanoma, either alone or in a combination therapy with one or more other therapeutic agents such as an MDM2 inhibitor. For example, the PKC inhibitor is Compound I or a pharmaceutically acceptable salt thereof. For example, the PKC inhibitor is suitable for administration at a dose of from about 100 mg to about 1000 mg of Compound I daily, e.g., via oral administration. For example, the PKC inhibitor is administered on an empty stomach, such as at least 1 hour before or 2 hours after a meal.

Any of the above aspects and embodiments can be combined with any other aspect or embodiment.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantage of the disclosure will be apparent from the following detailed description and claims.

DETAILED DESCRIPTION OF THE DISCLOSURE

Protein kinase C, specifically isoforms alpha and/or theta (PKCα/θ), has been found to play a role in certain disorders in a human or animal subject. The present disclosure relates to compounds, e.g., PKC inhibitors, that exhibit anti-proliferative activity when used alone and in combination, preferably in uveal melanoma (UM) patients. Suitably, the method relates to methods of treating a proliferative disease by administration or co-administration of said compounds.

In some embodiments, the PKC inhibitor as used herein can be 3-amino-N-(3-(4-amino-4-methylpiperidin-1-yl)pyridin-2-yl)-6-(3-(trifluoromethyl)pyridin-2-yl)pyrazine-2-carboxamide (Compound I) of formula I:

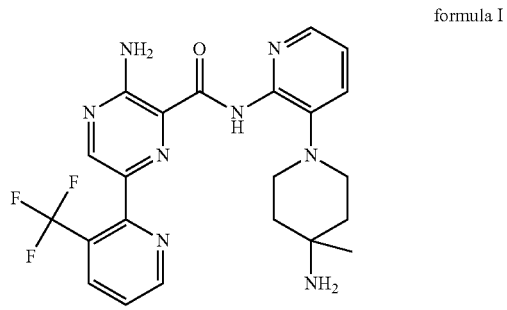 [SMILES: CC1(N)CCN(c2cccnc2NC(=O)c2nc(-c3ncccc3C(F)(F)F)cnc2N)CC1]

formula I (also known as LXS196). In some embodiments, the PKC inhibitor as used herein can be a pharmaceutically acceptable salt of Compound I.

In certain embodiments, Compound I or a pharmaceutically acceptable salt thereof is administered, e.g., orally administered at a dose of from about 100 mg to about 1000 mg of Compound I daily (e.g., about 100-800 mg or about 100-400 mg daily). For example, Compound I or a pharmaceutically acceptable salt thereof is administered at a dose of between about 50 mg twice a day (BID) and about 400 mg BID of Compound I (e.g., at a dose of about 50 mg BID, 100 mg BID, 150 mg BID, 200 mg BID, 250 mg BID, 300 mg BID, 350 mg BID, or 400 mg BID). As another example, Compound I or a pharmaceutically acceptable salt thereof is administered at a dose of from about 100 mg to about 1000 mg of Compound I once daily (e.g., about 400 mg, 500 mg, 600 mg, 700 mg or about 800 mg once daily).

In certain embodiments, Compound I or a pharmaceutically acceptable salt thereof is administered, e.g., orally administered at a dose of from about 1 mg/kg to about 25 mg/kg (e.g., between about 2 mg/kg to about 20 mg/kg, or between about 3 mg/kg to about 15 mg/kg, or between about 4 mg/kg to about 10 mg/kg) of Compound I daily based on the body weight of the subject. For example, Compound I or a pharmaceutically acceptable salt thereof is administered at a dose of between about 1 mg/kg twice a day (BID) and about 8 mg/kg BID of Compound I (e.g., at a dose of about 1 mg/kg BID, 2 mg/kg BID, 3 mg/kg BID, 4 mg/kg BID, 5 mg/kg BID, 6 mg/kg BID, 7 mg/kg BID, or 8 mg/kg BID). As another example, Compound I or a pharmaceutically acceptable salt thereof is administered at a dose of from about 2 mg/kg to about 20 mg/kg of Compound I once daily (e.g., about 3 mg/kg, 5 mg/kg, 8 mg/kg, 10 mg/kg, 12 mg/kg, 15 mg/kg, or 18 mg/kg once daily).

In certain embodiments, Compound I or a pharmaceutically acceptable salt thereof is administered at a dose that is therapeutically efficient while having little or no adverse effect. For example, said dose causes little or no hypotension. For example, about 5% or less (e.g., about 2.5% or less, 2% or less, 1% or less, or about 0.5% or less) patients administered with said dose experience hypotension of grade 3 or 4.

In certain embodiments, Compound I or a pharmaceutically acceptable salt thereof is administered on an empty stomach, such as at least 1 hour before or 2 hours after a meal. For example, water and other medications may be permitted during this period.

In other embodiments, Compound I or a pharmaceutically acceptable salt thereof is administered immediately prior to or after the subject eats some food.

In certain embodiments, Compound I or a pharmaceutically acceptable salt thereof is administered alone.

In certain embodiments, Compound I or a pharmaceutically acceptable salt thereof is administered with one or more other therapeutic agents, e.g., an anti-cancer agent.

In certain embodiments, Compound I or a pharmaceutically acceptable salt thereof is administered (either alone or in combination with another therapeutic agent) for a period of time (e.g., 1, 2, 3, 4, 5, 6, 7, 8, 9, 10, 11, 12, 13, or 14 days, specifically for example, administered daily for 7 days) at a lower dose immediately prior to treatment of a pharmaceutical combination comprising Compound I or a pharmaceutically acceptable salt thereof and one or more other therapeutic agents, e.g., an anti-cancer agent.

The present disclosure, relates also to a pharmaceutical combination, especially a pharmaceutical combination product, comprising, e.g., Compound I or a pharmaceutically acceptable salt thereof and one or more of other therapeutic agents described herein, and at least one pharmaceutically acceptable carrier.

In certain embodiments, the uveal melanoma or metastatic uveal melanoma comprises functional p53 or wild-type TP53. In other embodiments, the uveal melanoma or metastatic uveal melanoma comprises mutated TP53.

The protein p53 is a transcription factor that controls the expression of a multitude of target genes involved in DNA damage repair, apoptosis and cell cycle arrest, which are all important phenomena counteracting the malignant growth of tumors. The TP53 gene is one of the most frequently mutated genes in human cancers, with approximately half of all cancers having inactivated p53. Furthermore, in cancers with a non-mutated TP53 gene, typically the p53 is functionally inactivated at the protein level. One of the mechanisms of p53 inactivation is through its interaction with human homolog of MDM2 (Mouse double minute 2) protein. MDM2 protein functions both as an E3 ubiquitin ligase, that leads to proteasomal degradation of p53, and an inhibitor of p53 transcriptional activation. Therefore, MDM2 is an important negative regulator of the p53 tumor suppressor. MDM2 inhibitors can prevent interaction between MDM2 and p53 and thus allow the p53 protein to exert its effector functions. Whilst TP53 mutations are not common in UM, there are reports suggesting the p53 pathway is inactivated by either high expression of MDM2 protein or downregulation of the PERP protein in UM patients (Davies et al., Cell Death Dis. 2011 March; 2(3): e136).

A combination of an MDM2 inhibitor (Nutlin-3) has been shown to act synergistically with reactivation of p53 and induction of tumor cell apoptosis (RITA) and Topotecan to cause growth inhibition in UM cell lines (De Lange J. et al., Oncogene. 2012; 31:1105-16). However, Nutlin-3 and Topotecan delayed in vivo tumor growth only in a limited manner.

In some embodiments, the PKC inhibitor as used herein can be used in a combination therapy with one or more other therapeutic agents, such as a mouse double minute 2 inhibitor (MDM2i or HDM2i). By targeting the PKC pathway, either alone or in combination with p53, the PKC inhibitors disclosed herein or pharmaceutical compositions thereof and pharmaceutical combinations provided herein have been surprisingly found to be useful in treating UM or metastatic UM. The pharmaceutical compositions and pharmaceutical combinations and/or drug regimens described herein led to the induction of cell death in vitro, tumor stabilization and even tumor regression in vivo, with a surprisingly high in vivo tumor shrinkage observed in one combination.

The MDM2 inhibitor suitable for the methods, pharmaceutical compositions and/or pharmaceutical combinations described herein can be (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Compound II) of formula II:

formula II

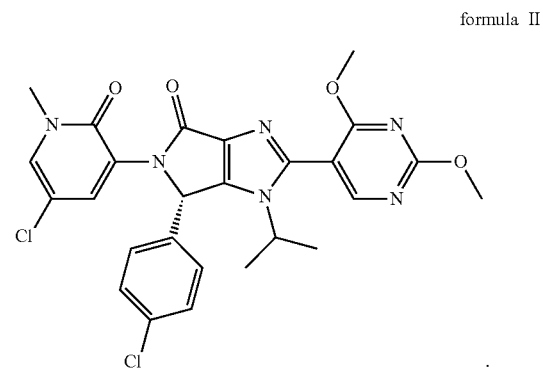 [SMILES: COc1ncc(-c2nc3c(n2C(C)C)[C@H](c2ccc(Cl)cc2)N(c2cc(Cl)cn(C)c2=O)C3=O)c(OC)n1]

The compound of formula II can be prepared as described in WO2013/111105.

The MDM2 inhibitor suitable for the methods, pharmaceutical compositions and/or pharmaceutical combinations described herein can also be (S)-1-(4-chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one (compound III) of formula III:

formula III

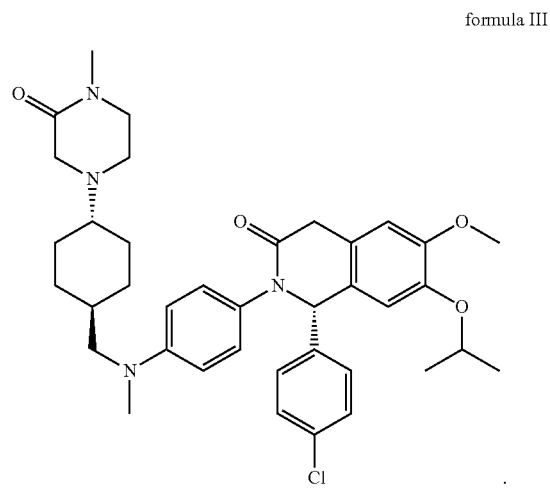 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2]

Compound III can be prepared as described in WO2011/076786. In one embodiment, the pharmaceutically acceptable salt of Compound III is a bisulphate salt. Crystalline form of the bisulfate salt of Compound III is described in WO2012/066095.

Other MDM2 inhibitors suitable for the methods, pharmaceutical compositions and/or pharmaceutical combinations described herein can also be those known by a skilled artisan, such as peptide MDM2 inhibitors, chlorofusin, spiro-oxindoles, Nutlins, benzodiazepinediones, NU8231, NU8354, NSC-66811, or $N^1$-(2-(1H-indol-3-yl)ethyl)-$N^4$-(pyridin-4-yl)benzene-1,4-diamine (see, e.g., Sharmila Patel & Mark R Player (2008) Small-molecule inhibitors of the p53-HDM2 interaction for the treatment of cancer, Expert Opinion on Investigational Drugs, 17:12, 1865-1882, which is incorporated herein in its entirety).

The present disclosure encompasses embodiments that include all pharmaceutically acceptable salts of the compounds useful according to the disclosure provided herein. As used herein, "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety. For example, preferred pharmaceutically acceptable salts include, but are not limited to, mineral or organic acid salts of basic residues such as amines. For example, the salt can be a sulphate salt, or bisulphate salt.

The compounds disclosed herein, particularly Compound I, may be in a form of a pharmaceutically acceptable prodrug. The term "pharmaceutically acceptable prodrugs" as used herein refers to those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the disclosure. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen, carbon, nitrogen, oxygen, fluorine, and chlorine, such as $^3$H, $^{11}$C, $^{13}$C, $^{14}$C, $^{15}$N, $^{18}$F, and $^{36}$Cl. Accordingly, it should be understood that the present disclosure includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds can generally be prepared by conventional techniques known to those skilled in the art, e.g., using an appropriate isotopically-labeled reagents in place of the non-labeled reagent previously employed.

The compounds described herein, e.g., a PKC inhibitor and/or a MDM2 inhibitor, can be used in combination, especially for use in a pharmaceutical combination that may optionally include further co-agents as defined below. All of these materials may be referred to as "active ingredients" in the combination. It should be understood that both terms (e.g., compound(s) and active ingredient(s)) encompass pharmaceutically acceptable salts, prodrugs, tautomers, N-oxides, or solvates, e.g., hydrates, of these materials. It should be understood when reading this disclosure that the combination disclosed herein encompasses all the aforementioned variants, as well as any single one thereof or combination of two or more to less than all such variants.

In certain embodiments, the uveal melanoma can also be metastatic UM. The compounds, methods, and/or combinations described herein can also be used to target metastasis of UM. Particularly, the combination of the disclosure is suitable for treatment of a patient with UM or metastatic UM, wherein the UM comprises functional p53 or wild-type TP53. Such protein or gene status of a cancer is expected to make a patient with said cancer even more responsive to the combination of the present disclosure. Equally, further improved effect of the combination is expected in uveal melanoma or metastatic uveal melanoma, including metastasis thereof, which is characterized by mutation in either GNAQ or GNA11 genes. In patients harboring both, the functional p53 or wild-type TP53 and mutation in either GNAQ or GNA11 genes, the clinical response is expected to be pronounced the most. Therefore, the pharmaceutical combination of the present disclosure is best suited for use in the treatment of a patient with UM or metastatic UM, including UM metastasis, wherein the UM comprises functional p53 or wild-type TP53 and is characterized by mutation in either GNAQ or GNA11 genes.

The term "pharmaceutical combination" as used herein means a product that results from the use or mixing or combining of more than one active ingredient. It should be understood that pharmaceutical combination as used herein includes both fixed and non-fixed combinations of the active ingredients. The term "fixed combination" means that the active ingredients, e.g., a compound of formula I and one or more combination partners, are administered to a patient simultaneously as a single entity or dosage form. The term in such case refers to a fixed dose combination in one unit dosage form (e.g., capsule, tablet, or sachet). The terms "non-fixed combination" or a "kit of parts" both mean that the active ingredients, e.g., a compound of the present disclosure and one or more combination partners and/or one or more co-agents, are administered or co-administered to a patient independently as separate entities either simultaneously, concurrently or sequentially with no specific time limits wherein such administration provides therapeutically effective levels of the two compounds in the body of the patient, especially where these time intervals allow that the combination partners show a cooperative, e.g., an additive or synergistic effect. The term "non-fixed combination" also applies to cocktail therapy, e.g., the administration of three or more active ingredients. The term "non-fixed combination" thus defines especially administration, use, composition or formulation in the sense that the compounds described herein can be dosed independently of each other, i.e., simultaneously or at different time points. It should be understood that the term "non-fixed combination" also encompasses the use of a single agent together with one or more fixed combination products with each independent formulation having distinct amounts of the active ingredients contained therein. It should be further understood that the combination products described herein as well as the term "non-fixed combinations" encompasses active ingredients (including the compounds described herein) where the combination partners are administered as entirely separate pharmaceutical dosage forms or as pharmaceutical formulations that are also sold independently of each other. Instructions for the use of the non-fixed combination are or may be provided in the packaging, e.g., leaflet or the like, or in other information that is provided to physicians and/or medical staff. The independent formulations or the parts of the formulation, products, or compositions, can then be administered simultaneously or chronologically staggered, that is the individual parts of the kit of parts can each be administered at different time points and/or with equal or different time intervals for any part of the kit of parts. Particularly, the time intervals for the dosing are chosen such that the effect on the treated disease with the combined use of the parts is larger/greater than the effect obtained by use of only one of the Compounds I-III; thus the compounds used in pharmaceutical combination described herein are jointly active. The ratio of the total amounts of a compound of formula I to a compound of formula II or III to be administered as a pharmaceutical combination can be varied or adjusted in order to better accommodate the needs of a particular patient sub-population to be treated or the needs of the single patient, which can be due, for example, to age, sex, body weight, etc. of the patients. For example, Compound I can be administered (e.g., orally) at a dose of 100 mg BID, 200 mg BID, 300 mg BID, or 400 mg BID in a 28 day cycle while Compound II is administered (e.g., orally) at a dose of 50 mg, 80 mg, 100 mg or 120 mg once weekly for 2 weeks followed by 2 weeks off (Day 1 and Day 8 of every 28 day cycle). As yet another example, Compound I can be administered (e.g., orally) at a lower starting dose (a "run-in" dose), e.g., 50 mg or higher BID (e.g., 50 mg BID, 75 mg BID, 100 mg BID, 200 mg BID or 300 mg BID) for a period of time (e.g., first 7 days of every 28 day cycle) while compound II is administered at a dose of 50 mg, 80 mg, 100 mg, 120 mg once weekly for 2 weeks followed by 2 weeks off, Compound I is then administered (e.g., orally) at a dose higher than the run-in dose, e.g., 75 mg or higher BID (e.g., 200 mg BID, 300 mg BID or 400 mg BID) for the rest of days in every 28 day cycle while Compound II is administered (e.g., orally) at a dose of 50 mg, 80 mg, 100 mg or 120 mg once weekly for 2 weeks followed by 2 weeks off (Day 1 and Day 8 of every 28 day cycle). In one embodiment, the run-in dose of Compound I is 100 mg BID for 7 days and the dose of Compound I following the run-in period is 200 mg BID or higher (e.g., 200 mg BID, 300 mg BID or 400 mg BID) while compound II is administered at a dose of 50 mg, 80 mg, 100 mg, 120 mg once weekly for 2 weeks followed by 2 weeks off. In another embodiment, the run-in dose of Compound I is 200 mg BID for 7 days and the dose of Compound I in the combination therapy following the run-in period is 300 mg BID or higher (e.g., 300 mg BID or 400 mg BID) while compound II is administered at a dose of 50 mg, 80 mg, 100 mg, 120 mg once weekly for 2 weeks followed by 2 weeks off, The terms "co-administration" or "combined administration" or the like as utilized herein are meant to encompass the administration of one or more compounds described herein together with a selected combination partner to a single subject in need thereof (e.g., a patient or subject), and are intended to include treatment regimens in which the compounds are not necessarily administered by the same route of administration and/or at the same time.

The term "pharmaceutical composition" is defined herein to refer to a mixture (e.g., a solution or an emulsion) containing at least one active ingredient or therapeutic agent to be administered to a warm-blooded animal, e.g., a mammal or human, in order to prevent or treat a particular disease or condition affecting the warm-blooded animal.

The term "kit of parts" is defined herein to refer to, e.g., combination partners (i) and (ii) as defined herein, i.e., (i) at least one protein kinase C pathway inhibitor (PKCi), e.g., Compound I or a pharmaceutically acceptable salt thereof, and (ii) at least one MDM2i, e.g., Compound II or Ill, or a pharmaceutically acceptable salt thereof. The combination partners can be dosed independently or by use of different fixed combinations with distinguished amounts of the combination partners (i) and (ii), i.e., simultaneously or at different time points. The parts of the kit of parts can then e.g., be administered simultaneously or chronologically staggered, that is at different time points and with equal or different time intervals for any part of the kit of parts. The ratio of the total amounts of the combination partner (i) to the combination partner (ii) to be administered in the combined preparation can be varied, e.g., in order to cope with the needs of a patient sub-population to be treated or the needs of the single patient.

The combination partners in any disclosure embodiment are preferably formulated or used to be jointly (prophylactically or especially therapeutically) active. This means in particular that there is at least one beneficial effect, e.g., a mutual enhancing of the effect of the combination partners, in particular a synergism, e.g., a more than additive effect, additional advantageous effects (e.g., a further therapeutic effect not found for any of the single compounds), less side effects, a combined therapeutic effect in a non-effective dosage of one or both of the combination partners disclosed herein, and very preferably a clear synergism of the combination partners.

The term "jointly therapeutically active" or "joint therapeutic effect" means that when the therapeutic agents, e.g., the active ingredients, are administered either in a chronologically staggered manner, especially a sequence-specific manner at preferred time intervals, in a warm-blooded animal, especially a human, to be treated, show a preferably synergistic interaction (joint therapeutic effect). Whether this is the case can, inter alia, be determined by following the blood levels, showing that both compounds are present in the blood of the human to be treated at least during certain time intervals.

As used herein, the term "patient" or "subject" refers to an animal. Typically, the animal is a mammal. A patient also refers to for example, primates (e.g., humans), cows, sheep, goats, horses, dogs, cats, rabbits, rats, mice, fish, birds and the like. In certain embodiments, the patient is a primate. In yet other embodiments, the patient is a human.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical combination product according to the disclosure (as a fixed combination, or non-fixed combination or as a kit of parts, e.g., as a combination of a fixed combination and/or individual formulations for one or both combination partners or as kit of individual formulations of the combination partners) comprises the combination of the present disclosure and one or more pharmaceutically acceptable carrier materials (carriers, excipients, or the like). The pharmaceutical combination or the combination partners constituting it can be formulated for particular routes of administration such as oral administration, parenteral administration, and rectal administration, etc. In addition, the combination products of the present disclosure can be made up in a solid form (including without limitation capsules, tablets, pills, granules, powders or suppositories), or in a liquid form (including without limitation solutions, suspensions or emulsions). The combination products and/or their combination partners (compounds, active ingredients) can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

The present disclosure thus pertains to a combination product for simultaneous or sequential use, such as a combined preparation or a pharmaceutical fixed combination, or a combination of such preparation and combination.

In the combination therapies of the disclosure, the compounds useful according to the disclosure may be manufactured and/or formulated by the same or different manufacturers. Moreover, the combination partners may be brought together into a combination therapy: (i) prior to release of the combination product to physicians (e.g., in the case of a kit comprising the compound of the disclosure and the other therapeutic agent); (ii) by the physician themselves (or under the guidance of a physician) shortly before administration; (iii) in the patient themselves, e.g., during sequential administration of the compound of the disclosure and the other therapeutic agent.

The information about the present combination or the use thereof in the treatment of uveal melanoma as described above and below can be shown on a data carrier, such as for example a product information leaflet, a summary of product characteristics, a brochure, marketing material, a web page, or when such information is stored or used on a data carrier such as for example a computer, an USB stick or a CD. Data carrier comprising information about using (i) a PKCi and (ii) an MDM2i is disclosed. The data carrier, for example in a form of a product information leaflet or a label, packaging, brochure or web page instruction can be used to instruct to administer (i) a PKCi of formula I, or a pharmaceutically acceptable salt thereof, and (ii) an MDM2i of formula II or Ill, or a pharmaceutically acceptable salt thereof, simultaneously or sequentially for the treatment of cancer. The data carrier is particularly useful in the event the two partners of the combination are not formulated together, and supplied or sold separately. Each of the partners can be supplied with the data carrier, or even have the data carrier detached or provided separately, that informs or instructs about the possibility to use the combination partner in a pharmaceutical combination of the present disclosure. The data carrier can be used for the same purpose also in fixed combinations or situations, where both partners are supplied or sold together.

In certain embodiments, any of the above pharmaceutical combination, use, administration, composition, method, product or formulation involves further administering one or more other (e.g., third) co-agents.

Thus, the disclosure also relates in a further embodiment to a pharmaceutical combination, particularly a pharmaceutical composition or a product comprising a therapeutically effective amount of (i) a PKCi and (ii) an MDM2i, respectively, and at least one third therapeutically active agent (herein referred to as an "additional co-agent"), e.g., another active ingredient. The additional co-agent is preferably selected from the group consisting of an anti-cancer agent and an anti-inflammatory agent, particularly is an anti-cancer agent.

The term "a therapeutically effective amount" of a compound (e.g., chemical entity or biologic agent) of the present disclosure refers to an amount of the compound of the present disclosure that will elicit the biological or medical response of a subject, for example, reduction or inhibition of an enzyme or a protein activity, or ameliorate symptoms, alleviate conditions, slow or delay disease progression, or prevent a disease, etc. The therapeutically effective dosage of a compound, the pharmaceutical composition, or the combinations thereof, is dependent on the species of the subject, the body weight, age, sex, and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

In certain embodiments, Compound II or III can be generally administered in unit dosage of about 1-5000 mg of active ingredient(s) for a subject of about 50-70 kg, or about 1 mg-3 g or about 1-250 mg or about 1-150 mg or about 0.5-100 mg, or about 1-50 mg of active ingredient. The unit dosage may be administered once or repeatedly during the same day, or during the week. For example, daily dose of between 15 mg/kg and 60 mg/kg (e.g., 30 mg/kg for injection or 50 mg/kg for oral administration), or daily dose of between 100 mg and 1500 mg (particularly between 300 mg and 1000 mg, e.g., 500-800 mg, 500 mg, or 800 mg) may be suitable for Compound III. For Compound II, doses between about 10 mg and 1000 mg may be suitable. The weekly dose between about 50 mg and 200 mg, particularly between about 75 mg and 150 mg, preferably about 100-120 mg, is expected to be efficacious for Compound I. Doses of the compounds may require drug holidays. For example, the dosing regimen may include 3 weeks on the drug and 1 week off, 2 weeks on and 2 weeks off, or 1 week on and 3 weeks off. The combination partners may not be administered according to the same dosing regimen. For example, Compound I can be administered daily (once, twice, or multiple times daily) while Compounds II or III can be administered once weekly, every 3 weeks or every 4 weeks. For example, Compounds II can be administered at, e.g., a dose of 120 mg at day 1 and 120 mg at day 8 (or alternatively on day 6, 7, 9, or 10) in a treatment cycle that lasts 28 days (4 weeks).

More examples of MDM2 inhibitors and dosing regimens (e.g., those for Compound II) suitable for the methods, compositions, and combinations of the disclosure are described in the Applications U.S. Ser. No. 62/422,144 filed Nov. 15, 2016 and 62/479,391 filed on Mar. 31, 2017, the contents of each of which are incorporated herein by reference in their entireties.

Unless otherwise specified, the weight or dosage referred to herein for a particular compound (e.g., any of Compounds I-III) of the disclosure is the weight or dosage of the compound itself, not that of a salt or prodrug thereof, which can be different to achieve the intended therapeutic effect. For example, the weight or dosage of a corresponding salt of a compound suitable for the methods, compositions, or combinations disclosed herein may be calculated based on the ratio of the molecular weights of the salt and compound itself.

The combination partners (e.g., the individual compounds described herein) that together form a corresponding pharmaceutical combination according to the disclosure may be mixed to form a fixed pharmaceutical composition or they may be administered separately or at approximately the same time (i.e., before, simultaneously with or after the other drug substance(s)).

The pharmaceutical compositions that comprise the pharmaceutical combination of the disclosure can be tablets or gelatin capsules comprising the active ingredient together with one or more commonly known carriers, e.g., one or more carriers selected from the group consisting of
  a) one or more diluents, e.g., lactose, dextrose, sucrose, mannitol, sorbitol, cellulose and/or glycine;
  b) one or more lubricants, e.g., silica, talcum, stearic acid, its magnesium or calcium salt and/or polyethyleneglycol; for tablets also
  c) one or more binders, e.g., magnesium aluminum silicate, starch paste, gelatin, tragacanth, methylcellulose, sodium carboxymethyl cellulose and/or polyvinylpyrrolidone; if desired
  d) one or more disintegrants, e.g., starches, agar, alginic acid or its sodium salt, or effervescent mixtures; and
  e) one or more absorbents, colorants, flavors and/or sweeteners.

Tablets may be either film coated or enteric coated according to methods known in the art.

Suitable compositions for oral administration especially include an effective amount of one or more or in case of fixed combination formulations each of the combination partners (active ingredients) in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient(s) in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Doses of Mdm2 inhibitors used in a composition may vary and is dependent for example on the route of administration, gender of a patient, weight, stadium of a disease, etc.

Parenteral compositions and other can be prepared by known methods in the art.

The use of the articles "a", "an", and "the" in both the description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of".

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 10% more or less than the specified value. In another embodiment, the term "about" refers to a range of values which are 5% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the terms "between X and Y" and "range from X to Y, are inclusive of X and Y and the integers there between. On the other hand, when a series of individual values are referred to in the disclosure, any range including any of the two individual values as the two end points is also conceived in this disclosure. For example, the expression "a dose of about 100 mg, 200 mg, or 400 mg" can also mean "a dose ranging from 100 to 200 mg", "a dose ranging from 200 to 400 mg", or "a dose ranging from 100 to 400 mg".

The following Examples illustrate the disclosure and provide specific embodiments, however without limiting the scope of the disclosure.

EXAMPLES

Example 1: A Phase I Trial of Compound I, a PKC Inhibitor for the Treatment of Uveal Melanoma A phase 1, multicenter, open-label, single-arm study of Compound I was performed in patients with metastatic uveal melanoma. A Bayesian logistic regression model, employing the escalation with overdose control principle, was used to guide the dose escalation and to estimate the maximum tolerated dose (MTD)/recommended dose for expansion (RDE). Safety was described using incidence of adverse events (AEs) by relation and severity of the AE graded according to the Common Terminology Criteria for AEs (CTCAE, v4.03). Overall response rate was defined as per Response Evaluation Criteria in Solid Tumors (RECIST, v1.1).

Patients eligible for inclusion in this study have to meet all of the following key criteria:
  Metastatic uveal melanoma (histologically or cytologically confirmed) that is judged to be progressive; patients may be treatment naive or have had any number of lines of prior therapy.
  Measurable disease, defined as at least one lesion that can be accurately measured in at least one dimension (longest diameter to be recorded) as >20 mm with conventional techniques or as >10 mm with CT scan.
  ECOG performance status ≤1

Patients eligible for this study must not meet any of the following criteria:
  Malignant disease other than that being treated in this study
  Symptomatic or untreated leptomeningeal or brain metastases or spinal cord compression. Treated brain metastases must have been stable for at least 1 month.
  Impaired cardiac function or clinically significant cardiac diseases
  Patients with abnormal laboratory values as defined by the protocol
  Systemic anti-cancer therapy within 2 weeks of the first dose of study treatment. For cytotoxic agents that have major delayed toxicity, e.g. mitomycin C and nitrosoureas, and for anti-PD-1 or PD-L1 antibodies 4 weeks is indicated as the washout period. For patients receiving a CTLA-4 antagonist or vaccine as anticancer therapy, 6 weeks is indicated as the washout period. Patients must have recovered or stabilized from toxicities related to their previous treatment except for alopecia.

As of the data of Jun. 12, 2017, 55 patients received Compound I (i.e., LXS196) at doses ranging from 100 mg to 1000 mg once daily (QD; 38 patients or "pts") and 200 mg to 400 mg twice daily (BID; 17 pts). Dose limiting toxicities (DLTs) were reported in 7 of 38 pts (QD schedule) and in 1 of 12 pts (BID schedule). The most common DLT was hypotension, manageable with LXS196 interruption and dose reduction. MTDs were determined at 500 mg QD and 400 mg BID. Due to better overall tolerability the RDE is 300 mg BID. Most common AEs (all grade, in ≥20% of pts) suspected related to LXS196 in pts across both schedules (n=55) were nausea (58.2%), diarrhea (32.7%), vomiting (25.5%), hypotension (25.5%), fatigue (20%) and asthenia (20%). The majority of GI and constitutional AEs were grade (gr) ½. Gr ¾ AEs suspected related to LXS196 were reported in 12 pts (21.8%), the most common being hypotension (10.9%). All other gr ¾ AEs occurred in ≤2 pts (3.6%) each. BID was better tolerated than QD dosing with fewer gr ¾ AEs (5.9% with BID vs 28.9% with QD dosing).

Pharmacokinetic (PK) studies demonstrated rapid absorption of LXS196 with $T_{max}$ of ~1 hr post dose and moderate elimination with consistent terminal $T_{1/2}$ across different doses (~10 hrs). Exposure at doses above 300 mg QD and 200 mg BID is in the efficacious range from preclinical projections. LXS196 led to reduction of phosphorylated myristoylated, alanine-rich C kinase substrate (pMARCKS) and phosphorylated PKC delta (pPKC delta), evident of target engagement in on-treatment tumor biopsies.

In 68 evaluable pts, 6 had confirmed partial responses (PR) per RECIST v 1.1 (300 mg QD, 500 mg QD, 200 mg BID, 2 at 300 mg BID, 400 mg BID). A further 45 pts had stable disease as best overall response. Preliminary data suggest encouraging clinical activity of LXS196 as monotherapy with manageable toxicities in pts with metastatic UM. The single-agent part of the study has completed enrolment.

Example 2: Combination Therapy of Compound I with MDM2i

The anti-tumor activity and tolerability of Compound I (i.e., LXS196) and the MDM2 inhibitor (Compound III or its salt thereof) was investigated in vivo using two patient derived uveal melanoma xenograft models, MP46 (GNAQmut) and MP55 (GNA11mut/BAP1 null).

MP46 and MP55 uveal melanoma tumors were established in female SCID mice by subcutaneous implantation of 3×3×3 mm tumor fragments into the flank of each mouse. When tumors reached approximately 100 mm³, mice were randomized according to tumor volume into treatment groups (n=8-10/group). Test agents were administered orally once (QD) or twice daily (BID) at the dose levels indicated. Tumor volumes of treatment groups are plotted from the time the treatment groups were randomized, and dosing commenced.

Combined oral treatment of LXS196 with Compound III led to increased depth of tumor response compared to either single agent in both models. In the MP46 model, Compound III dosed at 100 mg/kg QD achieved 39% treatment/control (T/C), while LXS196 dosed at 120 mg/kg BID achieved 63% regression, 35 days post dosing. The combination of LXS196 (dosed at 120 mg/kg BID) with Compound III (dosed at 100 mg/kg QD) achieved further improvements in anti-tumor response, achieving 97% regression. In the MP55 model, both LXS196 dosed at 120 mg/kg BID and Compound III dosed at 100 mg/kg QD achieved 20% T/C. In contrast, the combination of LXS196 and Compound III led to a 95% regression, 28 days post dosing. Collectively, these data suggest that combined treatment with LXS196 and Compound III may achieve greater and more durable responses in patients with uveal melanoma.

Efficacy of the combination of Compounds I and II was tested in the UM 92.1 cell line. The combination resulted in synergistic anti-proliferative effects (synergy score=2.24). See WO2017/029588, which is incorporated herein by reference.

Other Embodiments

While the invention has been described in conjunction with the detailed description thereof, the foregoing description is intended to illustrate and not limit the scope of the invention, which is indicated by the scope of the appended claims. Other aspects, advantages, and modifications are within the scope of the following claims. All changes that come within the meaning and range of equivalency of the claims are intended to be embraced therein.

The invention claimed is:

1. A method for treating uveal melanoma comprising administering to a subject in need thereof 3-amino-N-(3-(4-amino-4-methylpiperidin-1-yl)pyridin-2-yl)-6-(3-(trifluoromethyl)pyridin-2-yl)pyrazine-2-carboxamide (Compound I) or a pharmaceutically acceptable salt thereof at a dose of between about 100 mg BID and about 400 mg BID of Compound I daily.

2. The method of claim 1, wherein Compound I or a pharmaceutically acceptable salt thereof is administered at a dose of about 100 mg BID, 150 mg BID, 200 mg BID, 250 mg BID, 300 mg BID, 350 mg BID, or 400 mg BID.

3. The method of claim 2, wherein the dose is about 300 mg BID of Compound I.

4. The method of claim 1, wherein the subject suffers from metastatic uveal melanoma.

5. The method of claim 1, wherein the subject is an adult patient aged 18 years or older.

6. The method of claim 1, wherein Compound I or a pharmaceutically acceptable salt thereof is orally administered.

7. The method of claim 1, further comprising administering to the subject one or more other therapeutic agents.

8. The method of claim 1, wherein the uveal melanoma comprises functional p53 or wild-type TP53.

9. The method of claim 1, wherein the uveal melanoma is characterized by mutation of guanine nucleotide-binding protein G(q) subunit alpha (GNAQ) gene or guanine nucleotide-binding protein G(q) subunit 11 (GNA11) gene.

10. The method of claim 2, wherein the dose is about 400 mg BID of Compound I.

11. The method of claim 7, wherein the one or more other therapeutic agents is a mouse double minute 2 inhibitor (MDM2i) selected from (S)-5-(5-chloro-1-methyl-2-oxo-1,2-dihydro-pyridin-3-yl)-6-(4-chloro-phen-yl)-2-(2,4-dimethoxy-pyrimidin-5-yl)-1-isopropyl-5,6-dihydro-1H-pyrrolo[3,-4-d]imidazol-4-one (Compound II), (S)-1-(4-chlorophenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2-H-isoquinolin-3-one (Compound III), and pharmaceutically acceptable salts thereof.

12. The method of claim 2, wherein the dose is about 100 mg BID of Compound I.

13. The method of claim 2, wherein the dose is about 150 mg BID of Compound I.

14. The method of claim 2, wherein the dose is about 200 mg BID of Compound I.

15. The method of claim 2, wherein the dose is about 250 mg BID of Compound I.

16. The method of claim 2, wherein the dose is about 350 mg BID of Compound I.

* * * * *